United States Patent [19]

Shirrod et al.

[11] Patent Number: 5,714,832
[45] Date of Patent: Feb. 3, 1998

[54] MINIATURE GRATING DEVICE

[75] Inventors: Terry S. Shirrod; Dean H. S. Liskow, both of Albuquerque; John P. Blackburn, Rio Rancho, all of N. Mex.

[73] Assignee: Hughes Electronics, Los Angeles, Calif.

[21] Appl. No.: 616,899

[22] Filed: Mar. 15, 1996

[51] Int. Cl.$^6$ .................. H01L 41/08; H02N 2/00
[52] U.S. Cl. .................. 310/328; 310/330; 310/332
[58] Field of Search .................. 310/328, 330, 310/332

[56] References Cited

U.S. PATENT DOCUMENTS

| | | | |
|---|---|---|---|
| 3,684,904 | 8/1972 | Galutva et al. | 310/328 |
| 4,453,103 | 6/1984 | Vishnevsky et al. | 310/323 |
| 4,625,559 | 12/1986 | Carter et al. | 73/706 |
| 4,947,077 | 8/1990 | Murata | 310/328 |
| 5,259,032 | 11/1993 | Perkins et al. | 381/68 |
| 5,455,477 | 10/1995 | Sano et al. | 310/328 |

*Primary Examiner*—Thomas M. Dougherty
*Attorney, Agent, or Firm*—W. C. Schubert; W. K. Denson-Low

[57] ABSTRACT

A miniature grating drive device (216) for accurately and precisely positioning a grating (236) of a projection Moiré topography measurement system where the Moiré topography measurement system is included as part of a hand-held medical instrument for providing surface measurements of inaccessible living membranes. The drive device (216) includes two separate piezoelectric bimorph actuators (248, 256) for positioning the grating (236) at three precise locations. The first piezoelectric bimorph actuator (256) accurately positions the grating (236) at a first location, and the second piezoelectric bimorph (248) actuator accurately positions a base (232) on which the first piezoelectric actuator (256) is attached to move the grating (236) to a second location.

18 Claims, 4 Drawing Sheets

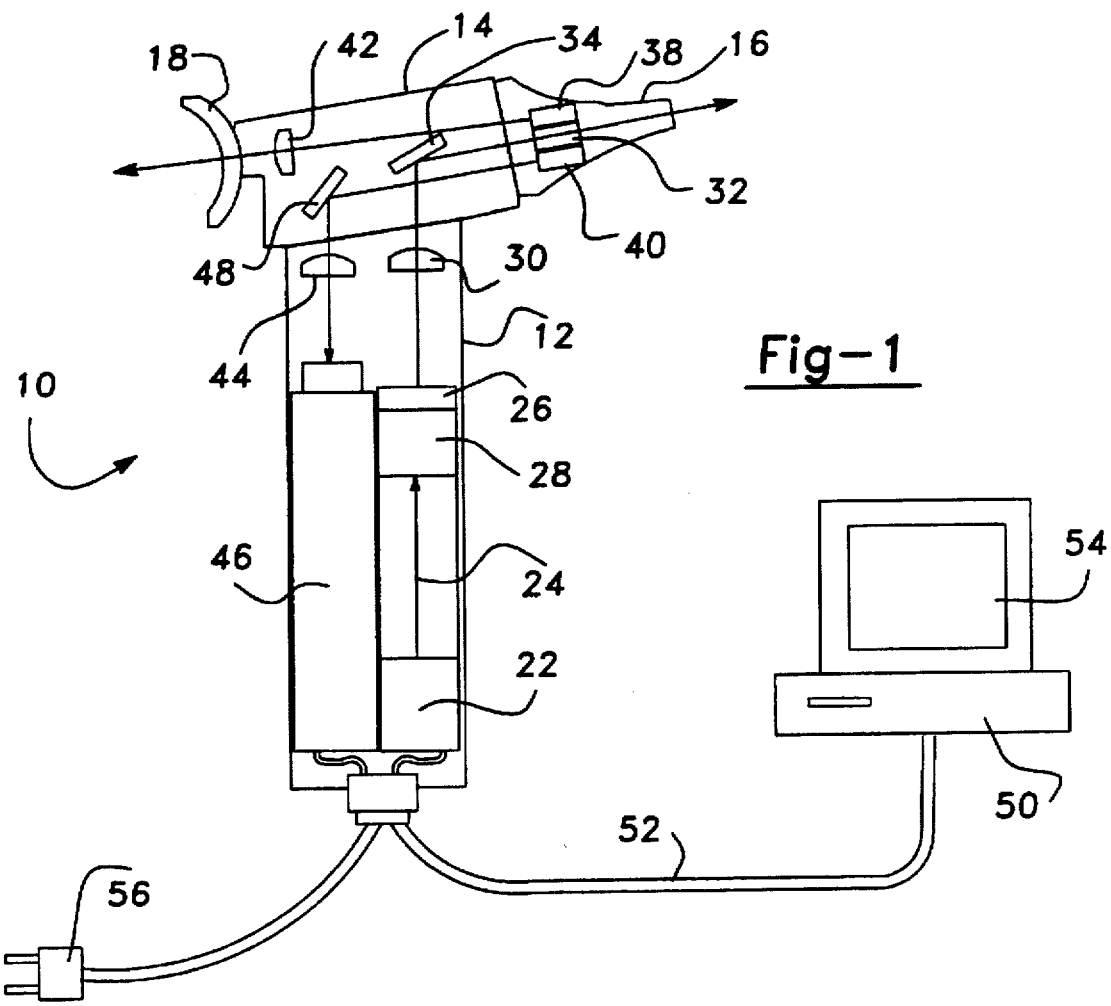
Fig-1
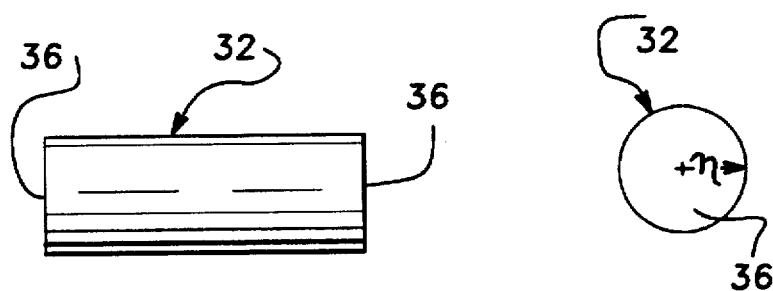
Fig-2a
Fig-2b

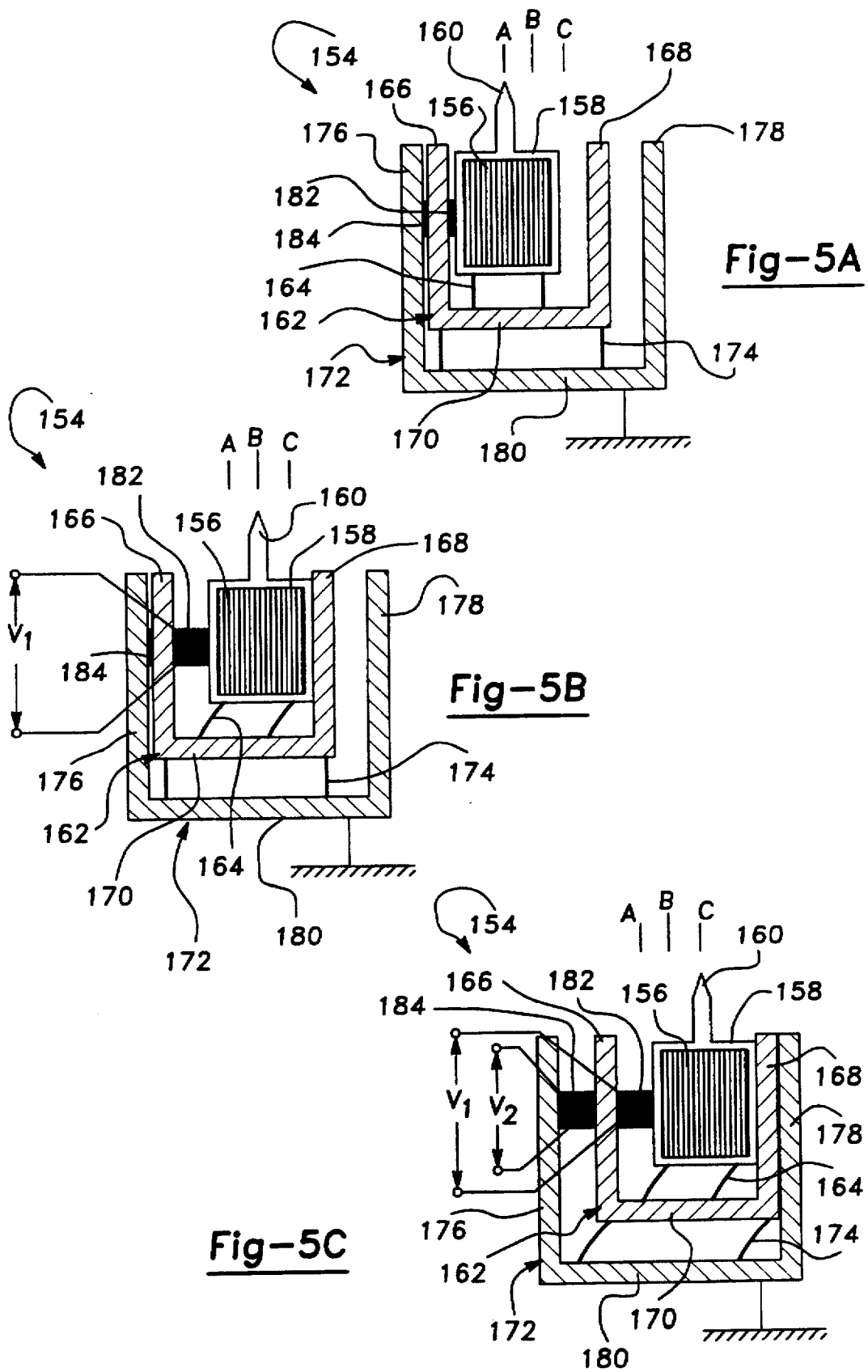

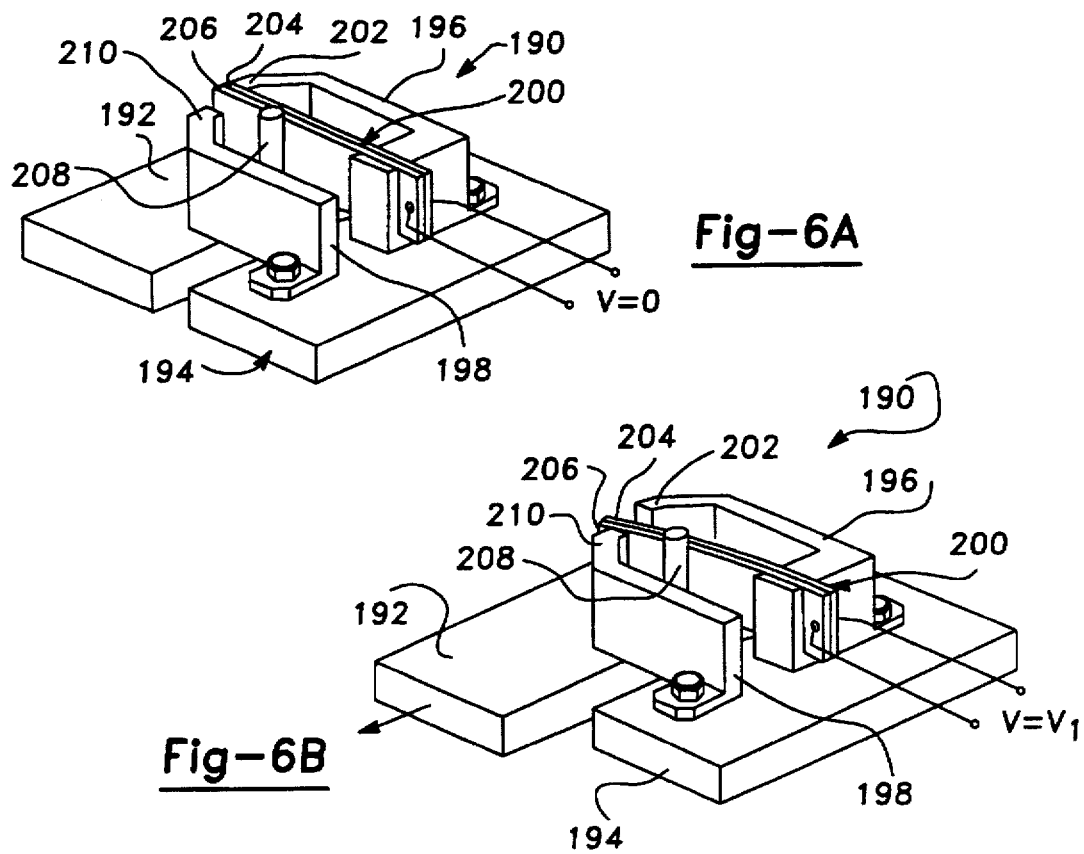
Fig-6A
Fig-6B
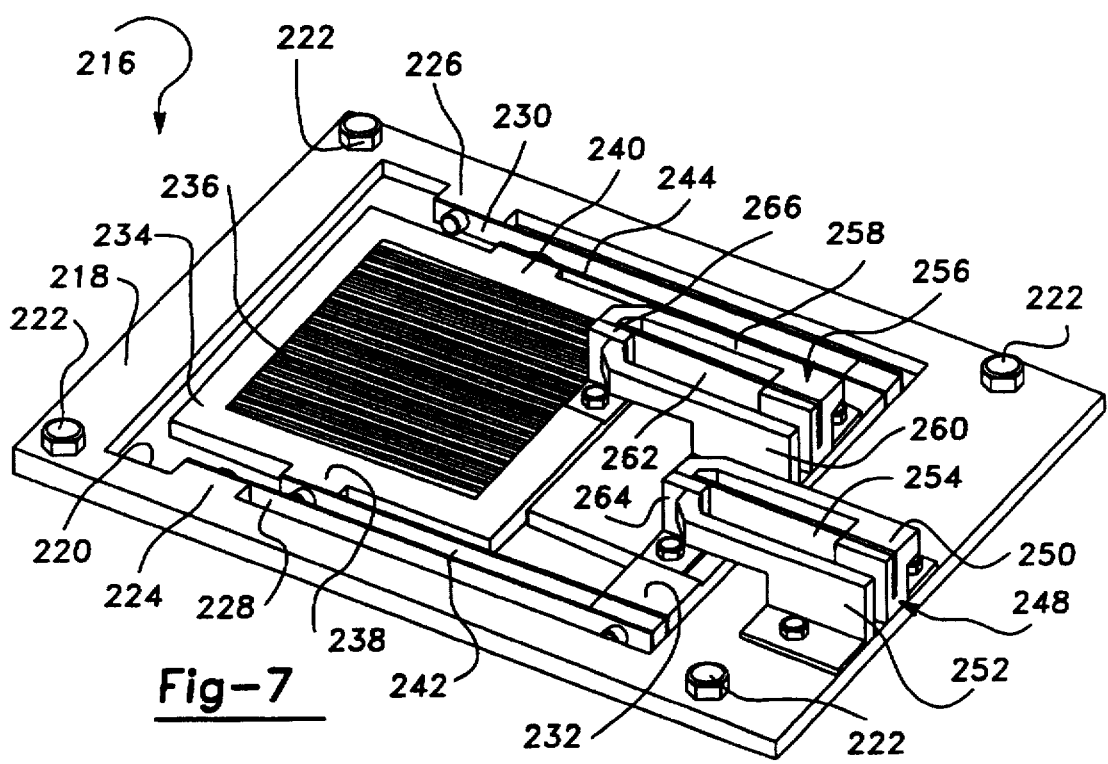
Fig-7

MINIATURE GRATING DEVICE

CROSS-RELATED APPLICATIONS

U.S. patent application Ser. No. (Attorney Docket PD-D95013) titled Quantitative Otoscopy Non-Invasive Metrology of the Ear and U.S. patent application Ser. No. (Attorney Docket No. PD-D94545) titled Hand-Held Moiré Topographic Instrument for Shape Measurement, being filed concurrently herewith and being assigned to the assignee of the instant application, are both related to the instant application.

BACKGROUND OF THE INVENTION

1. Field of the Invention

This invention relates generally to a miniature actuator and, more particularly, to a miniature piezoelectric actuator for driving a grating associated with a non-invasive otoscope.

2. Discussion of the Related Art

Otitis Media or inflammation of the middle ear, generally caused by bacterial infection, affects a large number of people, especially children under seven years of age. At the present time, physicians rely principally on a conventional otoscope, developed during the 19th century, to make their initial diagnosis of a patient who is affected by pain within the middle ear. In its simplest form, the conventional otoscope consists of an eye piece, a magnifying lens, a light source and a speculum all mounted on an otoscope body containing a battery power supply. Light emitted by the light source and magnified by the magnifying lens can be reflected off of the tympanic membrane, a tissue barrier between the middle ear and the external ear canal, of the ear to enable the physician to view the tympanic membrane through the eye piece. An example of a conventional otoscope can be found in U.S. Pat. No. 4,643,171 issued to Riester Feb. 17, 1987.

During examination with an otoscope, the physician inserts the speculum of the otoscope into the external ear canal of the patient to visually examine the patient's tympanic membrane through the eye piece. During this examination, the physician gathers an impression of the shape of the tympanic membrane, in particular any displacement caused by fluid accumulation in the middle ear, evaluates the color of the tympanic membrane, in particular redness associated with dilation of blood vessels of the middle ear, and searches for perforations of the tympanic membrane and leakage of fluid into the external ear canal. In addition, the physician may evaluate the mobility of the tympanic membrane by squeezing a pneumatic bulb associated with the otoscope to change the pressure in the internal ear canal. The extent to which the tympanic membrane moves in response to this transient pressure change is then observed. During the examination, the physician may make handwritten notes about the patient's ear health, as viewed with the otoscope, to document the examination as part of the patient's medical record. Conventional otoscopy therefore involves purely subjective and qualitative evaluation of the patient's ear.

If the physician finds an indication of infection or other potential problems, he may recommend a particular course of therapy. Additional diagnostic tests may also be required including tympanometry. Tympanometry involves use of a tympanometer that measures the acoustic impedance of the entire tympanic membrane to detect the existence of perforations in the tympanic membrane, or abnormal negative pressure in the middle ear associated with infection. Such a procedure is commonly administered by an audiologist who specializes in procedures of this nature.

If the diagnosis is an infection of the middle ear, antibiotics are commonly prescribed for the patient. In many cases, however, antibiotics are prescribed when the diagnosis of an ear infection is questionable. It is likely that the use of antibiotics without clear signs of infection contributes to the growing world-wide problem of antibiotic resistant microorganisms. Quantitative evidence for the presence of infection would be a significant advance in diagnosis of this type.

Patients who have persistent middle ear problems are generally surgically treated by a specialist in otolaryngology. The specialist may implant pressure equalization tubes in the tympanic membrane of the patient to drain fluid from the middle ear space. The placement of pressure equalization tubes has been questioned by the insurance industry and by the medical profession because uniform objective criteria for the placement of tubes have not been established, and a percentage of tube placements may be unwarranted.

Analysis of current modes of practice in otoscopy suggest a need for improvements in the diagnosis of ear disease in a number of areas. These areas include static and dynamic quantitative measurements of the tympanic membrane, and record storage of the quantitative measurements. For examples of static measurements, the patient's ear should be evaluated with a non-invasive method that permits rapid collection of quantitative information on the characteristics of the tympanic membrane. An image of the surface of the tympanic membrane should be provided to detect displacements produced by either negative or positive pressure in the middle ear, bulges produced by tumors or fluid accumulating in the middle ear space, and size and location of perforations in the tympanic membrane. Also, the color of the tympanic membrane, which reddens as blood vessels dilate in response to infection, should also be measured. For dynamic measurements, a visual display of the displacement of the tympanic membrane in response to calibrated changes in external ear canal pressure should also be provided. This is equivalent to a two-dimensional display of the compliance of the tympanic membrane to establish local changes in the mobility of the tympanic membrane, and provide information about the underlying cause of any change in mobility. Data and images of the tympanic membrane should be stored on a magnetic media to replace handwritten notes in order to supplant subjective impressions as the basis for diagnosis. The stored information would allow the physician to track the patient's condition from visit to visit, produce documentation for the choice of therapy, and be compatible with electronic data transmission for expert consultation at remote sites.

What is needed then is a modern medical instrument for a practical clinical environment that allows for real time static and dynamic observations of an inaccessible living membrane, such as a tympanic membrane, and provides simultaneous record storage of the observations and visualization of the membrane by a physician.

A Moiré pattern is a pattern of curves that results when at least two separate original patterns of curves are superimposed on each other. By moving one of the pattern of curves relative to the other pattern of curves, it has been shown that accurate measurements of minute displacements can be measured by the resulting Moiré pattern. Projection Moiré topography is a contour measurement technique using a ruled grating to produce a Moiré pattern that has been shown to be applicable to measure the topographical contours of living membranes. For discussions of projection Moiré topography of this type, see for example, Takasaki, H., "Moiré Topography", APPLIED OPTICS, Vol. 9, No. 6, June 1970, pp. 1467–1472; Takasaki, Hiroshi, "Moiré Topography from its Birth to Practical Application,"0 Optics and Lasers in Engineering, 3 (1982) pp. 3–14; Dirckx, J. J. J. et al., "Phase Shift Method Based on Object Translation for Full Field Automatic 3-D Surface Reconstruction from Moiré Topograms," APPLIED OPTICS, Vol. 27, No. 6, Mar. 15, 1988, pp. 1164–1169, Dirckx, Joris J. J., et al., "Automatic Calibration Method for Phase Shift Shadow Moiré Interferometry," APPLIED OPTICS, Vol. 29, No. 10, Apr. 1, 1990, pp. 1474–1476; and Takeda, Mitsuo et al., "Fourier Transform Profilometry for the Automatic Measurement of 3-D Object Shapes," APPLIED OPTICS, Vol. 22, No. 24, Dec. 15, 1983, pp. 3977–3982.

In projection Moiré topography of this type, one or more light sources are used to project a lined grating onto an object whose shape is to be measured to form light and dark fringes on the object. A grating drive system moves the grating a small amount in the plane of the grating to three phase stepped positions relative to the period of the grating lines. Phase-stepped images of the grating are reflected off of the object, and are captured by an optical sensor along a different optical axes to produce parallax in the sensed image. The position of the reflected images of the grating at each position are distorted by the difference in range between different locations on the surface of the object and the sensor. The relative range of an array of points on the surface of the object may be reconstructed by unwrapping phase information in the reflected images of the grating with respect to a designated origin. Range data of the array of points can be used to create a graphic display of a two-dimensional contour map of the surface of the object.

As set out in the above referenced articles describing Moiré topography, as well as other references in the literature, surface measurements of an object using Moiré topography is well documented in the art. These references document current methods of making measurements on the living or preserved ears of experimental animals, human cadaver ears or in some cases the living human ear. However, known surface measurement techniques of living membrane using projection Moiré topography utilize relatively large bench top instruments under laboratory conditions to measure the shape of the living membrane. These laboratory instruments have not been adapted for viewing small, inaccessible, unaugmented living tissue, such as the tympanic membrane, in a clinical environment. Also, data resulting from the contour measurements is generally processed over periods of hours or days. In no known projection Moiré topography technique, has optical measurements of the contour, range and motion of the tympanic membrane, or other living membrane, been made in near real time with a hand-held instrument which permits simultaneous visualization of the membrane.

Furthermore, laboratory Moiré analysis of living membranes generally require that the membrane be contrast—enhanced with, for example, white paint, to improve the diffuse reflectivity of the membrane. Additionally, Moiré topography instruments required that movement of the living membrane be restrained during measurement. All of these requirements are not desirable or practical for measuring surface topography of a living membrane of a patient during a clinical examination.

For a hand-held medical instrument, such as an otoscope, that utilizes projection Moiré topography for providing optical measurements of the contour, range and motion of a living membrane, it is necessary that the instrument provide precise and accurate positioning of a diffraction grating to produce phase-step images of the grating on the living membrane. In order to position the grating at the different locations, a grating drive device must be incorporated that accurately positions the grating so that movement of the medical instrument and movement of the living membrane during the measurements does not affect the accuracy of the measurements. Positioning systems for miniature optics of this nature which meet these requirements are not currently available.

It is one object of the present invention to provide a miniature drive device that is applicable to be used in a medical instrument where minute movements of a grating associated with a phase-stepped projection Moiré topography system is necessary, and where the grating drive device negates movement of the medical instrument and living membrane during measurements of the membrane.

SUMMARY OF THE INVENTION

In accordance with the teachings of the present invention, a miniature piezoelectric drive mechanism is disclosed. The drive mechanism in this embodiment includes at least one actuator having a base member, a first limit stop and a second limit stop where the first and second limit stops are secured to the base member. A payload is positioned adjacent to the base member and is movable relative to the base member. An elongated member extends from the payload between the first and second limit stops. A piezoelectric actuating mechanism is secured to the base member and extends adjacent to the elongated member. Activation of the piezoelectric actuating mechanism applies pressure to the elongated member to move the payload. The payload will move under the influence of the actuating mechanism until the actuating mechanism contacts the second limit stop.

In one particular embodiment, the miniature grating drive mechanism is associated with a hand-held medical instrument that provides surface measurements of an inaccessible living membrane, such as a tympanic membrane. The drive mechanism in this embodiment includes two separate piezoelectric bimorph actuators for positioning a grating associated with a projection Moiré topography systems at three precise locations. The first piezoelectric bimorph actuator accurately positions the grating at a first location, and the second piezoelectric bimorph actuator accurately positions a base on which the first piezoelectric actuator is attached to move the grating to a second location.

Additional objectives, advantages and features of the present invention will become apparent from the following description and appended claims made in conjunction with the accompanying drawings.

BRIEF DESCRIPTION OF THE DRAWINGS

FIG. 1 is a diagrammatic plan view of an otoscope according to an embodiment of the present invention;

FIG. 2(a) is a side view and FIG. 2(b) is an end view of a gradient index lens associated with the otoscope of FIG. 1;

FIGS. 5(a)–5(c) depict diagrammatic views of a model grating drive device according to an embodiment of the present invention;

FIGS. 6(a)–6(b) show perspective views of a piezoelectric bimorph actuator for use in a miniature grating drive device of the invention; and FIG. 7 shows a perspective view of a miniature grating drive device employing piezoelectric bimorph actuators according to the invention.

DETAILED DESCRIPTION OF THE PREFERRED EMBODIMENTS

Figure 3:
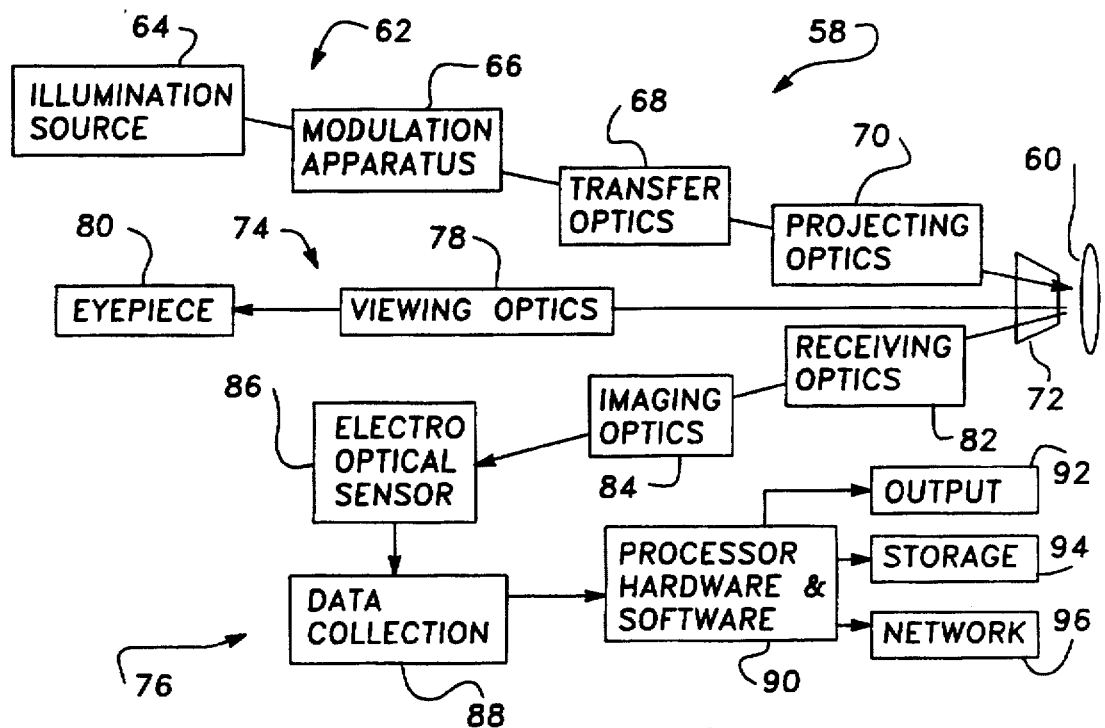
FIG. 3 is a block diagram depicting the operation of three optical paths within the otoscope of FIG. 1.

The following description of the preferred embodiments directed to a projection Moiré topography otoscope to measure the contours of a living membrane is merely exemplary in nature and is in no way intended to limit the invention or its applications or uses.

First turning to FIG. 1, a diagrammatic view of a quantitative otoscope 10 according to an embodiment of the present invention is shown. The otoscope 10 includes a hollow cylindrical body 12 attached to an optical head 14. A plastic speculum 16 is connected to one end of the optical head 14 and a rubber eye piece 18 is connected to an opposite end of the optical head 14. The otoscope 10 is of the size and shape of conventional otoscopes known in the art. The speculum 16 is inserted into a patient's ear canal (not shown), so a physician can view the patient's ear canal and tympanic membrane through the eye piece 18. Additionally, as will become apparent from the discussion below, the otoscope 10 includes a number of features that allow the physician to provide a quantitative analysis of the health of the patient's middle ear area.

The otoscope 10 includes an illumination source 22 positioned within the otoscope body 12. The illumination source 22 can be any applicable illumination source known in the art suitable for the purposes described herein, and preferably is a non-coherent, inexpensive white light source. The illumination source 22 emits an optical beam 24 that propagates through a lined grating 26. In one embodiment, the grating 26 is a Ronchi ruling, known to those skilled in the art, having equally spaced transparent and opaque stripes. A precision grating drive device 28 is connected to the grating 26 to provide stepped positional movements of the grating 26 during measurements. As will be discussed in greater detail below, for each measurement of the patient's tympanic membrane, the grating 26 is precisely and rapidly positioned to three different locations, where the difference between the locations is based on a fraction of the period of the lines in the grating 26.

The optical beam 24 then impinges an objective lens 30 to be focused onto a gradient index (GRIN) lens 32 after being bent by folding optics 34 in the optical head 14, as shown. The GRIN lens 32 projects and focuses the grating onto the patient's tympanic membrane through the speculum 16. The projected grating on the tympanic membrane provides a pattern of light and dark fringes on the membrane that has a phase dependent on the spacing of the grating lines of the grating 26 and the shape of the membrane.

A GRIN lens is a known lens that provides light focusing by an optical material having a varying index of refraction. FIG. 2(a) shows a side view and FIG. 2(b) shows an end view of the GRIN lens 32. The GRIN lens 32 is a cylinder of an optical plastic or glass such that the index of refraction varies with the distance from the cylinder axis and where end faces 36 of the lens 32 are flat. The lens 32 is a converging lens where the outermost part of the cylinder has the lowest index of refraction and the innermost part has the highest index of refraction, such that the index of refraction η decreases from the innermost part to the outermost part.

Such a lens provides a number of advantages for the purposes of the present invention, including long lens lengths where the lens itself can be several centimeters long, so as to provide access into the ear canal. In the embodiment shown, the GRIN lens 32 has a length of about 5 cm and a total diameter of about 1 mm.

Light reflected from the tympanic membrane is collected in the speculum 16 and is focused by a GRIN lens 38 and a GRIN lens 40. Reflected light collected by the GRIN lens 38 is focused onto a viewing lens 42 to be observed by the physician through the eye piece 18. Reflected light collected by the GRIN lens 40 is focused by a camera lens 44 onto a TV camera 46 within the optical body 12 after being bent by folding optics 48 in the optical head 14. The camera 46 can be a charged coupled device (CCD) camera where an array of CCDs of the camera 46 measure the light intensity at a particular location to provide a series of pixels (picture elements) of the total image of the membrane. Cameras of this type provide a high degree of resolution and are well known to those skilled in the art. In this manner, the tympanic membrane of the patient's ear can be simultaneously viewed by the physician and recorded by the camera 46 in real time.

Light intensity information processed by the camera 46 is applied to a personal computer (PC) 50 through an electrical cable 52. Connected to the PC 50 is a video screen 54 that gives a near real time image of the contour, range, and motion by Moiré topography of the tympanic membrane during the examination. The PC 50 includes specialized signal processing software and hardware, discussed below, to carry out the extensive data manipulation required for optical metrology in the shortest possible time. Optical data is analyzed and displayed on the video screen 54 as a high resolution surface image of the tympanic membrane along with information of the color spectrum of the light reflected from an array of points on the membrane. This information may be saved as a hard copy from a printer (not shown) and as a digital file on a storage medium within the PC 50. The digital file including data and images becomes part of the patient's medical record.

In this embodiment, the otoscope 10 is powered by a plug-in power cable 56. Although conventional otoscopes are generally battery operated, the bulk of space within the body 12 is taken up by the illumination source 22, the drive device 28 and the camera 46. Therefore, the otoscope 10 is powered by an exterior power source in this example. If desirable, the length of the body 12 can be extended to incorporate a suitable battery pack. Additionally, the otoscope 10 can be powered by the PC 50 through the cable 52.

The invention thus far has been discussed with reference to an otoscope for observing and measuring the contours of the tympanic membrane of a patient. However, it is stressed that the invention has application to other living membranes, such as nose and throat membranes, in conjunction with other types of medical instruments used for these purposes. The invention has particular application for viewing living membranes where the entrance aperture to the membrane is below 5 mm. Although not shown, a switch would be provided to activate the system when the physician was ready to take measurements of the membrane.

FIG. 3 shows a block diagram 58 depicting the operation of the otoscope 10 along each of three different optical paths through the otoscope 10 when measuring the surface contours of a tympanic membrane 60. A projection path 62 includes an illumination source 64, representing the illumination source 22. The illumination source 64 may include different features for different applications including enhanced brightness, wavelength filters, stroboscopy, etc., as would be understood to those skilled in the art. A modulation apparatus 66 provides precision grating motion, for example amplitude modulation of the optical beam generated by the illumination source 64. Transfer optics 68 represents the different optical components, such as the objective lens 30 and the mirror 34. The transfer optics 68 may include suitable molded plastic optical components and diffractive optical components for transmitting the optical beam through the otoscope 10. Projecting optics 70 represents the GRIN lens 32 for focusing the optical beam 24 on the tympanic membrane 60 through a speculum 72.

Light reflected from the tympanic membrane 60 into the speculum 72 is transmitted along a viewing path 74 and a sensing path 76. The viewing path 74 includes viewing optics 78 intended to represent the GRIN lens 40 and the lens 42, and an eye piece 80 intended to represent the eye piece 18. The sensing path 76 includes receiving optics 82 representing the GRIN lens 36 and the mirror 46, and imaging optics 84 representing the camera lens 44. The reflected beam on the sensing path 76 is then sensed by an electro-optical sensor 86, such as the CCD camera 46. The electro-optical sensor 86 provides electrical signals for an array of pixels indicative of the reflection intensity of the reflected beam, and provides these electrical signals to a data collection unit 88 intended to represent the PC 50. Processor hardware and software 90 represents the internal processing devices within the PC 50 that provide appropriate signals to a series of output sources. These output sources include an output source 92, such as a video display or a hard copy, a storage output 94, such as a hard disk or a floppy disk, and a network output 96 such as a transmission to a remote source.

It is noted that the transfer optics 68, the viewing optic 78, the receiving optics 82 and the imaging optics 84 are intended to represent the optics necessary for transmitting the optical beam to the tympanic membrane 60, and the reflected beam from the tympanic membrane 60 to the eye piece 80 and the optical sensor 86. These optics may vary from otoscope to otoscope, or instrument to instrument, depending on the particular application. Therefore, these different optics may be different than those illustrated in FIG. 1 for alternative embodiments within the scope of the invention.

Contour measurements of an object by projection Moiré topography is well documented in the literature. Various techniques and concepts within the scope of Moiré topography provide surface shape measurements for a wide range of different objects. In projection Moiré topography, an appropriate lined grating is projected onto an object to be measured to create light and dark Moiré fringes on the object having a phase determined by the spacing of the grating lines and the shape of the object. A mathematical relationship of the phase of the fringe pattern can be generated with respect to the surface of the object. If the object were perfectly flat, the bright and dark fringe lines on the object would appear as straight lines. For an object that is not flat, the lines are bent, and the phase of the fringes are altered with respect to the mathematical relationship of the phase pattern of a flat object. This change can be measured as changes in the sensed intensity of the reflected optical beam. The phase of the fringe pattern created by the shape of the surface of the object can then be calculated and converted to range differences, thus giving a mathematical representation of the surface shape of the object. A more detailed discussion of this process can be found in the Tasaki, H. and the Dirckx, J. J. J., et al. articles referenced above.

Although the shape of an object can be measured by Moiré topography processes when the grating is at a single location, it has been shown in the literature that a much more accurate shape representation can be achieved by taking measurements of the object with the grating at three locations within the plane of the grating. It has been shown that the displacement of the grating should be a fraction of the period of the grating. By taking Moiré topography measurements at these three locations, three different representations of the object can be generated so that unknown quantities, such as reflectivity from the object and background noise, can be eliminated.

Several procedures in digital signal processing will be used to circumvent the fact that most of a tympanic membrane, with the exception of a cone-shaped zone near the umbo, reflects only a small percentage of incident light and has low intrinsic contrast. These procedures include brightness ratioing to compensate for non-uniform reflectance, non-linear digitization to improve the signal-to-noise ratio in phase data at the expense of amplitude data for large signals, and two-dimensional spatial filtering to create a band pass filter about the grating frequency to reduce noise.

Changes in the range of the tympanic membrane evoked by calibrated pneumatic stimuli in the ear canal can be measured to provide a two-dimensional map of tympanic membrane compliance. The relative range of an array of points on the surface of the tympanic membrane may be reconstructed by unwrapping phase information in the reflected images of the grating with respect to a designated origin. The range data for the array of points are used to create a graphic display of the surface of the tympanic membrane. This embodiment gives a topography measurement resolution of less than 100 µm.

Figure 4:
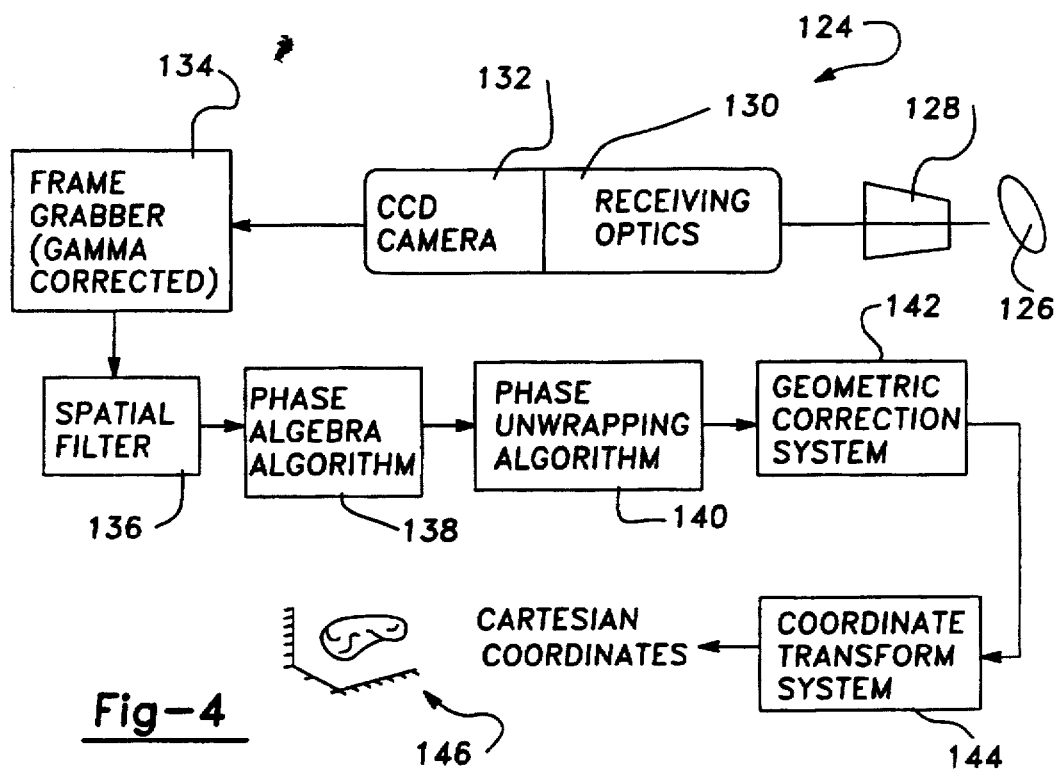
FIG. 4 is a block diagram depicting the operation of a projection Moiré topography technique for measuring the surface shape of a living membrane.

FIG. 4 shows a block diagram of the signal processing for projection Moiré topography of the invention that provides the above features. Reflected light from a tympanic membrane 126 is collected in a speculum 128 to be received by receiving optics 130. The receiving optics 130 focus the light onto a detector, such as a CCD camera 132. The CCD camera 132 generates electrical signals for each pixel of an image frame, and applies these signals to a frame grabber 134. The frame grabber 134 converts the electrical signals from the camera 132 into digital signals suitable for subsequent processing of the system. Further, the frame grabber 134 provides linearity correction (gamma correction) of the light intensity signals from the camera 132 in the event that the camera 132 is not a linear device. Spatial filtering from a spatial filter 136, such as a fast fourier transform (FFT) filter or a finite impulse response (FIR) filter, is then applied to the gamma corrected digital frame date that provides enhanced modulation of the grating image for noise filtering purposes, as is well understood in the art. The digital signals representing the frames of data from the spatial filter 136 are then applied to a phase algebra algorithm 138 to derive the modulation phase for each pixel in the image. The phase algebra system 138 generates the representative contour lines of the tympanic membrane 126 based on the phase of the grating for all of the pixels in the image, and provides a representative map of the object based on these phase differences.

The phase map signals are then applied to a phase unwrapping algorithm 140 to correct for phase discontinuities. The phase unwrapping system 140 reconstructs the relative range of an array of points on the surface of the membrane 126 and provides a continuous map of the tympanic membrane 126 so as to correct for ambiguities between adjacent cycles of the phase relationship of the grating lines projected on the tympanic membrane 126, as is well understood in the art. Spatial resolution of the array of points of the contour map will be at least 64×64 in this example.

The corrected phase signals are then applied to a geometric correction system 142 that applies non-linear phase correction to the signal. The geometric correction system 142 provides calibration to the signal as the result of beam expansion that may alter the phase function of the beam. An output of the geometric corrector 142 is in range and angle coordinates which are then converted to Cartesian coordinates by a coordinate transform system 144. The Cartesian coordinate system can then be displayed as a graphic surface display 146 showing the tympanic membrane 126. Each of the operations discussed above with reference to the frame grabber 134, the spatial filter 136, the phase algebra algorithm 138, the phase unwrapping algorithm 140, the geometric correction system 142 and the coordinate transform system 144 are all well known operations that can be performed in the hardware and software of the PC 50 of FIG. 1. The general operations are typical to known Moiré topography systems and would be well understood to those skilled in the art.

The discussion above has been directed to surface mapping of a tympanic membrane. However, the Moiré topography method of the invention, in conjunction with the associated optics, can be used to view and record any living membrane in association with a suitable device to provide real time analysis of the membrane. The Moiré topography method of the invention is particularly adaptable to real time clinical analysis of small, inaccessible membranes of the human body.

As discussed above, the grating drive device 28 must precisely position the grating 26 in three locations for each contour measurement for order to be practical for the otoscope 10, it must be small enough to fit easily within the otoscope body 12, and be relatively inexpensive. The grating drive device 28 must rapidly and accurately position the grating so that movement by the physician as he holds the otoscope 10, and movement of the tympanic membrane during measurement, do not affect the tympanic membrane shape calculations. In one example according to the invention, the grating drive device 28 displaces the grating 26 in three phase steps of 120° each at a rate of 16 msec or less per step. Therefore, the grating drive device 28 must be assembled from low-cost components that are small and reliable. Different systems can be devised to meet these requirements. In one embodiment, the grating drive device 28 may include liquid crystal displays that are electrically actuated to alter the grating line positions in a grating display. Other applicable grating drive systems make use of piezoelectric actuators.

FIGS. 5(a)–5(c) show a diagrammatic view of a grating drive 154 that can be used as the drive device 28 according to an embodiment of the present invention. The grating drive 154 includes a grating 156 positioned on a grating platform 158. A pointer 160 extends from the platform 158 to indicate at what location the grating 156 is positioned. The grating platform 158 is secured to an inner conductive cage 162 by a pair of resilient metal leaf springs 164 as shown. The inner cage 162 includes a left-side wall 166 and a right-side wall 168 connected to a base 170. The leaf springs 164 are connected to the platform 158 and the base 170 as shown. The inner cage 162 is secured to a grounded outer conductive cage 172 by a pair of resilient metal leaf springs 174 as shown. The outer cage 172 includes a left-side wall 176 and a right-side wall 178 connected to a base 180. The leaf springs 174 are connected to the base 170 of the inner cage 162 and the base 180 of the outer cage 172. The leaf springs 164 allow the grating platform 158 to be resiliently positioned at different locations within the inner cage 162. Likewise, the leaf springs 174 allow the inner cage 162 to be resiliently positioned at different locations within the outer cage 172.

A first piezoelectric actuator 182 is positioned between the left-side wall 166 of the inner cage 162 and the grating platform 158, and a second piezoelectric actuator 184 is positioned between the left-side wall 176 of the outer cage 172 and the left-side wall 166 of the inner cage 162. When both of the piezoelectric actuators 162 and 176 are in their relaxed state, i.e., no voltage potential is applied to the actuator 182 and 184, the grating platform 158 is positioned adjacent the left-side wall 166 within the inner cage 162, and the inner cage 162 is positioned adjacent the left-side wall 176 within the outer cage 166 as shown in FIG. 6(a). In this position, the leaf springs 164 and 174 are also in their relaxed state. At this location the pointer 160 indicates that the grating 156 is at position "A".

By grounding the outer cage 172 and applying a suitable voltage potential $V_1$ to the first actuator 182, the first actuator 182 expands against the resiliency of the leaf springs 164 such that the leaf springs 164 bend causing the grating platform 158 to move across the inside of the inner cage 162 and contact the right-side wall 168 of the inner cage 162, as shown in FIG. 6(b). When the grating platform 158 is in this position, the pointer 160 indicates that the grating 156 is at the "B" position. If the voltage $V_1$ is maintained on the piezoelectric actuator 182, and a suitable voltage potential $V_2$ is applied to the piezoelectric actuator 184, the actuator 184 will expand against the resiliency of the leaf springs 174 such that the leaf springs 174 bend causing the inner cage 162 to move towards the right within the outer cage 172 until the right-side wall 168 of the inner cage 162 contacts the right-side wall 178 of the outer cage 172, as shown in FIG. 6(c). When the inner cage 162 is in this position, the pointer 160 indicates that the grating 156 is positioned at location "C". In this manner, the grating 156 can be accurately positioned at three locations very rapidly for contour measurements. Note that the leaf springs 164 and 174 are "stiff" so that the grating 156 and the inner cage 162 return to their relaxed position when the voltage potential $V_1$ and $V_2$ are removed. One of ordinary skill in the art would know how to program the PC 50 to provide the voltage potentials $V_1$ and $V_2$ at the appropriate time to the drive 154 to position the grating 156 at the desirable locations during contour measurements.

It should be noted that a fourth position is also realizable by the drive 154. Particularly, if the voltage $V_1$ is removed and the voltage $V_2$ is maintained, the inside piezoelectric actuator 182 will be relaxed such that the grating platform 158 will move back to the left-side wall 166 of the inner cage 162. If the distance between the positions "A" and "B", and the distance between the positions "B" and "C" are not equal, then this fourth position may be a unique position relative to the position "B".

The drive 154 represents a model of a grating drive suitable for the purposes of the present invention. One of the difficulties encountered in recording multiple images of a living membrane is that the membrane tends to move between the time the different images are recorded. Similarly, an operator of the otoscope 10 may not be able to hold the otoscope 10 steady while recording the images. For this reason, the three images necessary for each contour measurement must be obtained rapidly in comparison to the movement speed of the membrane and the operator. This requirement implies that the grating drive must be capable of moving rapidly between the three required positions. Analysis has shown that the grating drive must be able to move the grating from one position to the next position in less than 1/60 of a second. While piezoelectric actuators which operate on the principle depicted in FIGS. 5(a)–5(c) are capable of providing this requirement, the stroke and force required for the drive 154 may necessitate an actuator size which may not be compatible with a hand-held otoscope.

Turning to FIGS. 6(a)–6(b), perspective views of a piezoelectric bimorph actuator 190 are shown. The actuator 190 includes a payload 192 movable relative to a base 194. A first rigid limit stop 196 is secured to the base 194 at one location, and a second rigid limit stop 198 is secured to the base 194 at a second location relative to each other, as shown. A piezoelectric laminate 200 is secured to the limit stop 196, and contacts a stop edge 202 of the limit stop 196 when the laminate 200 is in a relaxed state, i.e., when the voltage potential applied to the laminate 200 is zero as shown in FIG. 7(a). The piezoelectric laminate 200 includes a first piezoelectric layer 204 and a second piezoelectric layer 206 of two different piezoelectric materials that expand differently under the influence of an electric field. The piezoelectric layer 204 and the piezoelectric layer 206 can be any piezoelectric material, known in the art, suitable for the purposes of the present invention. The two piezoelectric layers 204 and 206 are rigidly secured to each other. A bumper post 208 is rigidly secured to the payload 192 between the limit stop 198 and the piezoelectric laminate 200, as shown. Piezoelectric laminates of the type of laminate 200 are known in other types of piezoelectric actuators, for example, piezoelectric actuators that are commercially available piezoelectric bimorph actuators from Morgan-Matrok of Bedford, Ohio.

A zero voltage potential applied to the laminate 200 positions the payload 192 relative to the base 194 as shown in FIG. 6(a). If a suitable voltage potential $V_1$ is applied to the laminate 200, then the piezoelectric layer 204 will expand more than the piezoelectric layer 206 such that the piezoelectric laminate 200 bends toward the limit stop 198, applying pressure against the bumper post 208. Pressure against the bumper post 208 causes the payload 192 to move in the direction of the arrow as shown in FIG. 6(b). The laminate 200 will eventually contact a stop edge 210 of the limit stop 198 so that the travel of the payload 192 is set by the position of the limit stop 198 so as to accurately position the payload 192 when the voltage potential is applied to the piezoelectric laminate 122. The movement of the payload 192 can be controlled by shaving the stop edge 210. In this manner, the payload 192 can be accurately and quickly positioned at different locations for different applications.

FIG. 7 shows a perspective view of a miniature grating drive (MGD) 216 according to an embodiment of the present invention. The MGD 216 includes an outer cage 218 defining an opening 220. A series of fasteners 222 enable the drive 216 to be secured in, for example, the otoscope body 12. A first tab member 224 and a second tab member 226 extend into the opening 220 as shown. A first outer leaf spring 228 and a second outer leaf spring 230 are secured to the tab members 224 and 226, respectively, and to an inner cage 232 positioned within the opening 220 as shown. A grating platform 234 holding a grating 236 is positioned within the opening 220 adjacent to the inner cage 232. The grating platform 234 includes a first tab member 238 positioned adjacent to the tab member 224 and a second tab member 240 positioned adjacent to the tab member 226. A first inner leaf spring 242 is secured to the tab member 238 and the inner cage 232, and a second inner leaf spring 244 is secured to the tab member 240 and the inner cage 232, as shown.

An outer piezoelectric bimorph actuator 248 includes a first limit stop 250, a second limit stop 252 and a piezoelectric laminate 254 where the limit stop 250 and the limit stop 254 are secured to the outer cage 218, and the piezoelectric laminate 254 is secured to the limit stop 250, as shown. An inner piezoelectric bimorph actuator 256 includes a limit stop 258, a limit stop 260, and a piezoelectric laminate 262 where the limit stop 258 and the limit stop 260 are secured to the inner cage 232, and the piezoelectric laminate 262 is secured to the limit stop 258 as shown. A retaining tab 264 is rigidly secured to the inner cage 232 and is positioned between the limit stops 250 and 252, as shown. Likewise, a retaining tab 266 is rigidly secured to the grating platform 234 and is positioned between the limit stops 258 and 260, as shown. The retaining tabs 264 and 266 operate to limit the travel of the piezoelectric laminates 254 and 262, respectively. The distance between the retaining tab 264 and the limit stop 252, and the retaining tab 266 and the limit stop 260 is small because the different positions of the grating 236 are close compared with the phase of the grating 236. The outer bimorph actuator 248 and the inner bimorph actuator 256 operate in the same manner as the piezoelectric bimorph actuator 190 discussed above.

When no voltage potential is applied to either of the piezoelectric laminates 254 and 262, the grating 254 is positioned at a first location. If a suitable voltage potential is applied to the piezoelectric laminate 262 and the piezoelectric laminate 254 has no potential applied to it, the piezoelectric laminate 262 will apply pressure against the retaining tab 266. Pressure against the retaining tab 266 will cause the platform 234 to move against the bias of the inner leaf springs 240 and 242. The platform 234 will continue to move until the retaining tab 266 contacts the limit stop 260, thus setting the position of a second location of the grating 236. If the voltage potential is removed from the piezoelectric laminate 262, the resiliency of the inner leaf springs 242 and 244 will return the grating 236 to its first location. If the voltage potential is maintained on the piezoelectric laminate 262, and a suitable voltage potential is applied to the piezoelectric laminate 254, the piezoelectric laminate 254 will apply pressure against the retaining tab 264. Pressure against the retaining tab 264 from the piezoelectric laminate 254 will cause the inner cage 232 to move against the resiliency of the outer leaf springs 228 and 230. Movement of the inner cage 232 also moves the grating platform 234. Pressure against the retaining tab 264 will cause the inner cage 232 to continue to move until the retaining tab 264 contacts the limit stop 252. This location sets the third location of the grating 236. In this manner, the MGD 216 can rapidly and accurately position the grating 236 at three locations suitable for contour mapping as discussed above.

The otoscope of the present invention can be used to establish standards of diagnosis for ear disease in published clinical trials, and other purposes by medical students, primary care physicians, general practitioners, pediatricians, internists and otolaryngologists worldwide. Practitioners can adopt the device to provide quantitative evidence for subjective diagnosis, for patient tracking and the maintenance of patient records, and to accumulate a local database on ear disease for research and clinical purposes. The ability to transmit images collected with the otoscope to remote sites at regional medical centers may be important to primary care physicians who may require expert consultation. Furthermore, the quantitative measurement of tympanic membrane compliance can be made optically by the physician without referral to an audiologist for a tympanometry, thus avoiding costs for an additional test at a separate site if such equipment is not available to the physician.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A drive device comprising:

a base member;

a first movable member positioned relative to the base member;

a second movable member positioned relative to the base member and the first movable member, said second movable member being selectively movable between a first location, a second location and a third location relative to the base member;

a first piezoelectric actuator rigidly secured to the first movable member and positioned relative to the second movable member, wherein the first piezoelectric actuator includes a first piezoelectric laminate having first and second piezoelectric layers, said first and second piezoelectric layers being of different piezoelectric materials so as to expand differently under the first voltage potential, said first piezoelectric actuator being responsive to a first voltage potential to cause the first piezoelectric actuator to position the second movable member from the first location to the second location; and a second piezoelectric actuator rigidly secured to the base member and positioned relative to the first movable member, wherein the second piezoelectric actuator includes a second piezoelectric laminate having third and fourth piezoelectric layers, said third and fourth piezoelectric layers being of different piezoelectric materials to expand differently under the second voltage potential, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location.

2. A drive device comprising:

a base member;

a first movable member positioned relative to the base member;

a second movable member positioned relative to the base member and the first movable member, said second movable member including a grating associated with a projection Moiré topography system, said grating being selectively movable and positionable between a first location, a second location and a third location relative to the base member so as to provide Moiré topography measurements of an object, wherein the second movable member includes;

a first piezoelectric actuator rigidly secured to the first movable member and positioned relative to the second movable member, said first piezoelectric actuator being responsive to a first voltage potential to cause the first piezoelectric actuator to position the second movable member from the first location to the second location; and a second piezoelectric actuator rigidly secured to the base member and positioned relative to the first movable member, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location.

3. The drive device according to claim 2 wherein the Moiré topography system is part of an otoscope that measures the contour of a tympanic membrane.

4. The drive device according to claim 2 wherein the first and second piezoelectric actuators position the object from the first location to the second location and from the second location to the third location in less than 1/60 of a second.

5. A drive device comprising:

a base member;

a first movable member positioned relative to the base member;

a second movable member positioned relative to the base member and the first movable member, said second movable member being selectively movable between a first location, a second location and a third location relative to the base member;

a first piezoelectric actuator rigidly secured to the first movable member and positioned relative to the second movable member, said first piezoelectric actuator being responsive to a first voltage potential to cause the first piezoelectric actuator to position the second movable member from the first location to the second location; and a second piezoelectric actuator rigidly secured to the base member and positioned relative to the first movable member, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location;

wherein the first piezoelectric actuator includes a first piezoelectric layer, a first limit stop and a second limit stop, said first piezoelectric layer being positioned against the first limit stop under no voltage potential, and being positioned against the second limit stop under the first voltage potential so as to accurately position the second movable member; and wherein the second piezoelectric actuator includes a second piezoelectric layer, a third limit stop and a fourth limit stop, said second piezoelectric layer being positioned against the third limit stop under no voltage potential, and being positioned against the fourth limit stop under the second voltage potential so as to accurately position the first and second movable members.

6. A drive device comprising:
   a base member;
   a first movable member positioned relative to the base member;
   a second movable member positioned relative to the base member and the first movable member, said second movable member being selectively movable between a fast location, a second location and a third location relative to the base member;
   a first piezoelectric actuator rigidly secured to the first movable member and positioned relative to the second movable member, said first piezoelectric actuator being responsive to a first voltage potential to cause the first piezoelectric actuator to position the second movable member from the first location to the second location; and
   a second piezoelectric actuator rigidly secured to the base member and positioned relative to the first movable member, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location;
   wherein the first piezoelectric actuator includes a first limit stop, a second limit stop and a first piezoelectric laminate positioned therebetween, said first piezoelectric laminate being rigidly secured to said first limit stop at a first end of the first piezoelectric laminate and a second end of the first piezoelectric laminate being free to move under the influence of the first voltage potential, said first piezoelectric actuator further including a first tab member rigidly secured to the second movable member and positioned between the first limit stop and the second limit stop adjacent the second end of the first piezoelectric laminate; and
   wherein the first voltage potential causes the second end of the first piezoelectric laminate to apply pressure against the first tab member to move the first tab member towards the second limit stop so as to contact the second limit stop and position the second movable member at the second location.

7. The drive device according to claim 6 wherein the second piezoelectric actuator includes a third limit stop, a fourth limit stop and a second piezoelectric laminate positioned therebetween, said second piezoelectric laminate being rigidly secured to said third limit stop at a first end of the second piezoelectric laminate and a second end of the second piezoelectric laminate being free to move under the influence of the second voltage potential, said second piezoelectric actuator further including a second tab member rigidly secured to the second movable member and positioned between the third limit stop and the fourth limit stop adjacent the second end of the second piezoelectric laminate, wherein the second voltage potential causes the second end of the second piezoelectric laminate to apply pressure against the second tab member to move the second tab member towards the fourth limit stop so as to contact the fourth limit stop and position the second movable member at the third location.

8. A drive device comprising:
   a base member;
   a first movable member positioned relative to the base member;
   a second movable member positioned relative to the base member and the first movable member, said second movable member being selectively movable between a first location, a second location and a third location relative to the base member;
   a first piezoelectric actuator rigidly secured to the first movable member and positioned relative to the second movable member, said first piezoelectric actuator being responsive to a first voltage potential to cause the first piezoelectric actuator to position the second movable member from the first location to the second location;
   a second piezoelectric actuator rigidly secured to the base member and positioned relative to the first movable member, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location; and
   at least one inner leaf spring and at least one outer leaf spring, said at least one inner leaf spring being rigidly secured to the first movable member and the second movable member, and said at least one outer leaf spring being rigidly secured to the first movable member and the base member, wherein actuation of the first piezoelectric actuator causes the second movable member to be positioned in the second position against the bias of the inner leaf spring, and actuation of the second piezoelectric actuator causes the first movable member to move the second movable member against the bias of outer leaf spring.

9. A drive device comprising:
   a base member, wherein the base member is an outer cage defining an opening;
   a first movable member positioned relative to the base member, said first movable member being a platform positioned within the opening and being secured to the outer cage by a first resilient member;
   a second movable member positioned relative to the base member and the first movable member, said second movable member being positioned within the opening adjacent to the first movable member and being connected to the first movable member by a second resilient member, said second movable member being selectively movable between a first location, a second location and a third location relative to the base member;
   a first piezoelectric actuator rigidly secured to the first movable member and positioned relative to the second movable member, said first piezoelectric actuator being responsive to a first voltage potential to cause the first piezoelectric actuator to position the second movable member from the first location to the second location; and
   a second piezoelectric actuator rigidly secured to the base member and positioned relative to the first movable member, said second piezoelectric actuator being responsive to a second voltage potential to cause the second piezoelectric actuator to move the first movable member, wherein movement of the first movable member causes movement of the second movable member such that when the first voltage potential is applied to the first piezoelectric actuator and the second voltage potential is applied to the second piezoelectric actuator the second movable member is positioned in the third location.

10. A drive device comprising:

a base member;

a first limit stop including a first end portion and a second end portion, said first end portion of said limit stop being secured to the base member;

a second limit stop including a first end portion and a second end portion, said first end portion of the second limit stop being secured to the base member adjacent to and spaced from the first end portion of the first limit stop;

a payload positioned relative to and separated from the base member, said payload being movable relative to said base member;

an elongated member rigidly secured to the payload and being positioned relative to the second end portion of the first limit stop; and an actuating mechanism including a first end portion and a second end portion, said first end portion of said actuating mechanism being rigidly secured to the base member and the second end portion of the actuating mechanism being positioned adjacent to the second end portion of the first limit stop and the elongated member, wherein the actuating mechanism is actuatable to apply pressure against the elongated member to move the payload relative to the base member, said second end portion of said second limit stop limiting the travel of the actuating mechanism and the payload.

11. The drive device according to claim 10 wherein the actuating mechanism is a piezoelectric bimorph including a first piezoelectric layer and a second piezoelectric layer, said first and second piezoelectric layers being of different piezoelectric materials such that when a voltage potential is applied to the piezoelectric bimorph, the first piezoelectric layer expands more than the second piezoelectric layer causing the piezoelectric bimorph to move towards the second limit stop.

12. The drive device according to claim 10 wherein the elongated member contacts the second limit stop under the influence of a driving pressure from the actuating mechanism.

13. The drive device according to claim 10 wherein the actuating mechanism contacts the second limit stop within 1/60 of a second after a voltage potential is applied to actuating mechanism.

14. A miniature drive device for driving an object comprising:

an outer cage defining an opening;

an inner cage positioned within the opening and being secured to the outer cage by a first resilient member, said inner cage being movable relative to the outer cage against a bias of the first resilient member;

a platform positioned within the opening adjacent to the inner cage and being connected to the inner cage by a second resilient member, said platform being movable relative to the inner cage and the outer cage against a bias of the second resilient member;

a first piezoelectric actuator rigidly secured to the outer cage and positioned relative to the inner cage, said first piezoelectric actuator including a first piezoelectric strip, a first limit stop and a second limit stop, said first piezoelectric strip being positioned against the first limit stop under no electrical potential and being positioned against the second limit stop under a first voltage potential, said first piezoelectric strip being responsive to the first voltage potential to cause the first piezoelectric actuator to position the inner cage against the bias of the first resilient member; and a second piezoelectric actuator rigidly secured to the inner cage and positioned relative to the platform, said second piezoelectric actuator including a second piezoelectric strip, a third limit stop and the fourth limit stop, said second piezoelectric strip being positioned against the third limit stop under no voltage potential and being positioned against the fourth limit stop under a second voltage potential, said second piezoelectric strip being responsive to the second voltage potential to cause the second piezoelectric actuator to position the platform against the bias of the second resilient member.

15. The drive device according to claim 14 wherein the first and second piezoelectric strips are piezoelectric laminates including two piezoelectric layers of a different piezoelectric material.

16. The drive device according to claim 14 wherein the platform is a grating platform holding a grating associated with a projection Moiré topography system, said grating being selectively positionable in a first, second and third location so as to provide Moiré topography measurements of an object.

17. The drive device according to claim 16 wherein the Moiré topography system is part of an otoscope that measures the contour of a tympanic membrane.

18. The drive device according to claim 16 wherein the first and second piezoelectric actuators position the grating from the first location to the second location and from the second location to the third location in less than 1/60 of a second.

* * * * *